United States Patent
Yang et al.

(10) Patent No.: US 10,093,682 B1
(45) Date of Patent: Oct. 9, 2018

(54) METHOD FOR SYNTHESIZING TETRAHYDROISOQUINOLINE OXAZOLIDINE

(71) Applicant: National Chi Nan University, Nantou County (TW)

(72) Inventors: Te-Fang Yang, Taichung (TW); Sheng-Han Huang, Taichung (TW); Yan-Liang Lin, Taichung (TW); Wen-Tse Huang, Taipei (TW); Yu-Wei Shih, Taichung (TW)

(73) Assignee: NATIONAL CHI NAN UNIVERSITY, Nantou County (TW)

( * ) Notice: Subject to any disclaimer, the term of this patent is extended or adjusted under 35 U.S.C. 154(b) by 0 days.

(21) Appl. No.: 15/653,991

(22) Filed: Jul. 19, 2017

(30) Foreign Application Priority Data

May 26, 2017 (TW) .............................. 106117569 A

(51) Int. Cl.
*C07D 498/04* (2006.01)

(52) U.S. Cl.
CPC .................. *C07D 498/04* (2013.01)

(58) Field of Classification Search
CPC .................................... C07D 498/04
IPC .................................. C07D 498/04
See application file for complete search history.

(56) References Cited

FOREIGN PATENT DOCUMENTS

TW    I243168 B   11/2005
TW    I324603 B   5/2010

OTHER PUBLICATIONS

Umetsu & Asao, 49 Tetrahedron Letts. 2722-2725 (2008) (Year: 2008).*
Huang et al., 6 RSC Adv., 91870-91874 (2016) (Year: 2016).*
Umetsu, K.et al; "An efficient method for construction of tetrahydroisoquinoline skeleton via double cyclization process using ortho-vinylbenzaldehydes and amino alcohols: application to the synthesis of (S)-cryptostyline II"; Tetrahedron; vol. 49, Issue 17, Apr. 21, 2008, pp. 2722-2725.
Yamato, M. et al: "Syntheses of chiral oxazolo [2,3-a] tetrahydroisoquinoline and its asymmetric alkylation. Synthesis of (S)-(−)- and (R)-(+)-salsolidines"; Tetrahedron Letters; vol. 29, Issue 52, 1988, pp. 6949-6950.
Ardill, H. et al; "X=Y-ZH compounds as potential 13-dipoles. Part 29. The iminium ion route to azomethine ylides. Reaction of cyclic secondary amines with mono- and bl-functional aldehydes"; Tetrahedron; vol. 46, Issue 18, 1990, pp. 6449-6466.

* cited by examiner

*Primary Examiner* — Timothy R Rozof
(74) *Attorney, Agent, or Firm* — Muncy, Geissler, Olds & Lowe

(57) ABSTRACT

The invention relates to a method for synthesizing tetrahydroisoquinoline oxazolidine. The method is carried out at a room temperature between 20° C. and 35° C.

10 Claims, No Drawings

METHOD FOR SYNTHESIZING TETRAHYDROISOQUINOLINE OXAZOLIDINE

FIELD OF THE INVENTION

The invention relates to a method for synthesizing tetrahydroisoquinoline oxazolidine, in particular to a method capable of synthesizing tetrahydroisoquinoline oxazolidine at normal temperature and under normal pressure.

BACKGROUND OF THE INVENTION

In recent years, micromolecules with an oxazolidine architecture have been proven to have effects of resisting tumors and inhibiting bacteria, and the potential medical value of the micromolecules with the oxazolidine architecture has been increasing year after year. Besides a method for separating and purifying the micromolecules with the oxazolidine architecture from natural products, in academic aspect, lots of scientists published various methods for synthesizing oxazolidine, and they try to use an artificial synthesizing mode to obtain natural products or novel oxazolidines micromolecules with a curative effect.

For example, an oxazolidinone anti-microbial compound is disclosed in Publication Patent Number 1324603 of the Republic of China, a chemical formula is as shown in the following formula (I). The compound is an anti-microbial agent with special activity, and can be used for resisting Gram-positive human and veterinary pathogens.

Formula (I)

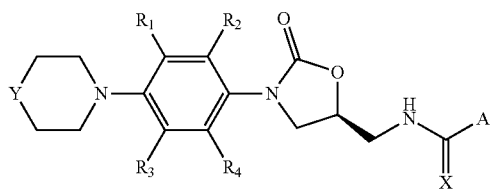

Alternatively, in order to obtain an oxazolidinones compound easily, in the aspect of a synthesizing method, an industrial preparation method for an oxazolidinone-2-one derivative, which is disclosed in Publication Patent Number 1243168 of the Republic of China, is used for obtaining the oxazolidinone-2-one derivative with the structure as shown in the following formula (II) by using a 1,2-diol derivative which is easily taken from a precursor of a 1,3-dioxolane-2-one derivative as a raw material. Because required steps are fewer when the 1,2-diol derivative which is easily obtained is converted into the oxazolidinone-2-one derivative, the preparation method is efficient; however, the synthesizing method needs to be carried out in the presence of villiaumite.

Formula (II)

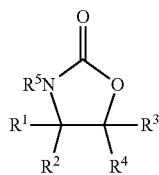

In addition, synthesis of an isoquinoline oxazolidines compound with a benzene ring on a main architecture can refer to the paper (Ardill, H.; Fontaine, X. L. R.; Grigg, R. Henderson, D.; Montgomery, J.; Sridharan, V.; Surendrakumar, S., Tetrahedron 1990, 46, 6449-6466.) which was published by Grigg in 1990. One equivalent of 1,2,3,4-tetrahydroisoquinoline reacteds with two equivalents of pyridine-2-carboxaldehyde, acetonitrile was used as a solvent to carry out heating reflux for three hours to obtain a 1,3-oxazolidine product as shown in the following formula (III).

Formula (III)

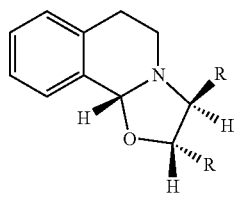

R = 2-pyridy

The paper (Yamato, M.; Hashigaki, K.; Ishikawa, S.; Qais, N. Tetrahedron Lett., 1988, 29, 6949-6950) which was published by Yamato in 2008 discloses that 2-(2-bromoethyl)-4,5-dimethoxybenzaldehyde is used as an initiator, carries out nucleophilic substitution reaction with (R)-phenylglycinol at first, and then is subjected to intramolecular cyclization reaction under the conditions of alkaline and low temperature to obtain a chiral oxazolidine isoquinoline isomer as shown in the following formula (IV).

Formula (IV)

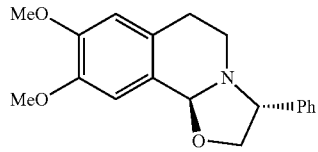

Moreover, the paper (Umetsu, K.; Asao, N. Tetrahedron Lett. 2008, 49, 2722-2725.) which was published by Asao in 2008 discloses that an initiator was ortho-vinylbenzaldehyde, after a compound (R)-phenylglycinol is subjected to substitution reaction at first, an intermediate of 2,3-dihydroisoquinoline is then obtained through 6-azaelectrocyclization, and finally intramolecular nucleophilic reaction is carried out to obtain a final product as shown in the following formula (V). An original reaction solvent was converted into dimethyl sulfoxide from 1,4-dioxane.

Formula (V)

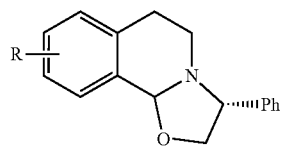

An existing synthesis method for isoquinoline oxazolidine is not perfect, for example, the synthesis method cannot be carried out at room temperature, or the synthesis method needs to be carried out in the presence of a catalyst, and application and development of the isoquinoline oxazolidines compound are limited. Therefore, a novel synthesis method still needs to be developed with great efforts, and by the novel synthesis method, the isoquinoline oxazolidines compound can be rapidly and efficiently obtained on the premise of not reducing the yield.

SUMMARY OF THE INVENTION

The main purpose of the invention is to overcome the shortcoming that a known oxazolidines compound, particularly an isoquinoline oxazolidines compound with a benzene ring on a main architecture, needs to be synthesized in virtue of a catalyst and a strict environment at high temperature or under a specific acid-base condition in a synthesis process. In order to achieve the purpose, the invention provides a method capable of synthesizing tetrahydroisoquinoline oxazolidine at normal temperature and under normal pressure, synthesis conditions are lenient, synthesis steps are quite simple, therefore, synthesis cost can be reduced, and the method conforms to a currently promoted green chemistry concept. The invention provides a method for synthesizing tetrahydroisoquinoline oxazolidine, comprising: reacting a compound 1a with a compound 1b, wherein the compound 1a is

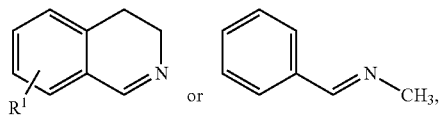

and $R^1$ is hydrogen, halogen, methyl group, alkoxy group or phenyl. Moreover, the compound 1b is In the compound 1b, $R^2$ is selected from a substituted or unsubstituted phenyl, a substituted or unsubstituted naphthalene, a substituted or unsubstituted straight chain alkyl, a substituted or unsubstituted straight chain alkenyl, a substituted or unsubstituted straight chain alkynyl, a substituted or unsubstituted branched chain alkyl, a substituted or unsubstituted branched chain alkenyl, or a substituted or unsubstituted branched chain alkynyl, and the method is carried out at a room temperature between 20° C. and 35° C.

In the prior known art, synthesis needs to be carried out in a strict environment or by adding a catalyst, but the method can be used for synthesizing the tetrahydroisoquinoline oxazolidine at normal temperature and under normal pressure by relatively few steps within relatively short time. Therefore, compared with the prior known art, the method has lenient synthesis conditions, but and also has quite simple synthesis steps, thus the synthesis cost can be effectively reduced, and the method also conforms to the currently promoted green chemical chemistry concept.

BRIEF DESCRIPTION OF THE DRAWINGS

No description.

DETAILED DESCRIPTION OF THE PREFERRED EMBODIMENTS

The detailed description and the technical content of the invention are described as follows with reference to experiments:

The invention provides a method for synthesizing tetrahydroisoquinoline oxazolidine, comprising: reacting a compound 1a with a compound 1b, wherein the compound 1a is wherein $R^1$ is hydrogen, halogen, methyl group, alkoxy group or phenyl.

The compound 1b is

In the compound 1b, $R^2$ is selected from a substituted or unsubstituted phenyl, a substituted or unsubstituted naphthalene, a substituted or unsubstituted straight chain alkyl, a substituted or unsubstituted straight chain alkenyl, a substituted or unsubstituted straight chain alkynyl, a substituted or unsubstituted branched chain alkyl, a substituted or unsubstituted branched chain alkenyl, or a substituted or unsubstituted branched chain alkynyl.

In the invention, the method is carried out at a room temperature between 20° C. and 35° C., and is preferably carried out at a room temperature between 20° C. and 30° C.

In an embodiment of the invention, an equation is as follows:

In an embodiment of the invention, R² can be a phenyl which is substituted by a substituent group, and the substituent group is selected from at least one of a group consisting of an alkoxy group, halogen, a nitro and a combination thereof more specifically, for example, R² can be a phenyl substituted by a methoxyl group; but in other embodiments, R² can also be a phenyl substituted by a nitro.

In an embodiment of the invention, reaction time required for the synthesis ranges from 10 minutes to 3 hours, and preferably ranges from 10 minutes to 1 hour. However, the reaction time may be slightly different along with difference of reaction conditions. For example, on the premise that the yield reaches 73% and additives are not added, if methylbenzene is used as a solvent, the reaction time is 1 hour, and if methanol is used as a solvent, the reaction time is 15 minutes.

In an embodiment of the invention, the compound 1a and the compound 1b react according to the equivalent proportion of 1:1, and therefore, the method can be carried out without accurate or complicated proportioning in an operation process, and has the advantage of convenience in operation.

In an embodiment of the invention, in order to increase reaction rate, an additive can be used, and for example, the additive can be acetic acid.

In an embodiment of the invention, when the compound 1a is a compound as shown in the following formula, the reaction is carried out in a solvent, and the solvent is selected from methylbenzene, ethyl acetate, ether, water, methanol, ethanol, butanol and a combination thereof:

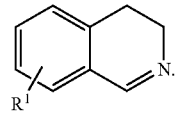

Hereby, a compound 1c which is synthesized from the compound 1a and the compound 1b through reaction by the method is selected from the following chemical structures:

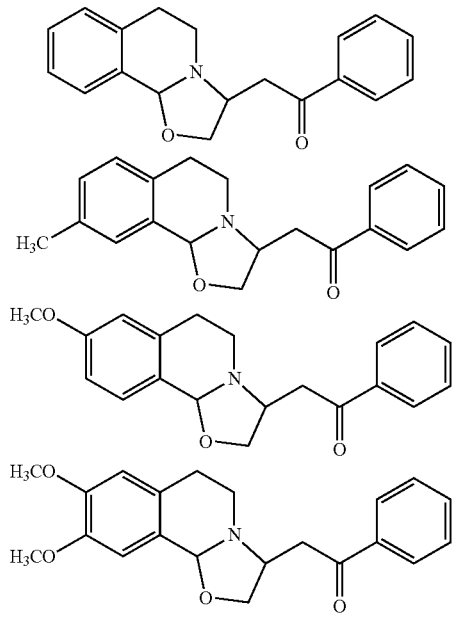

-continued

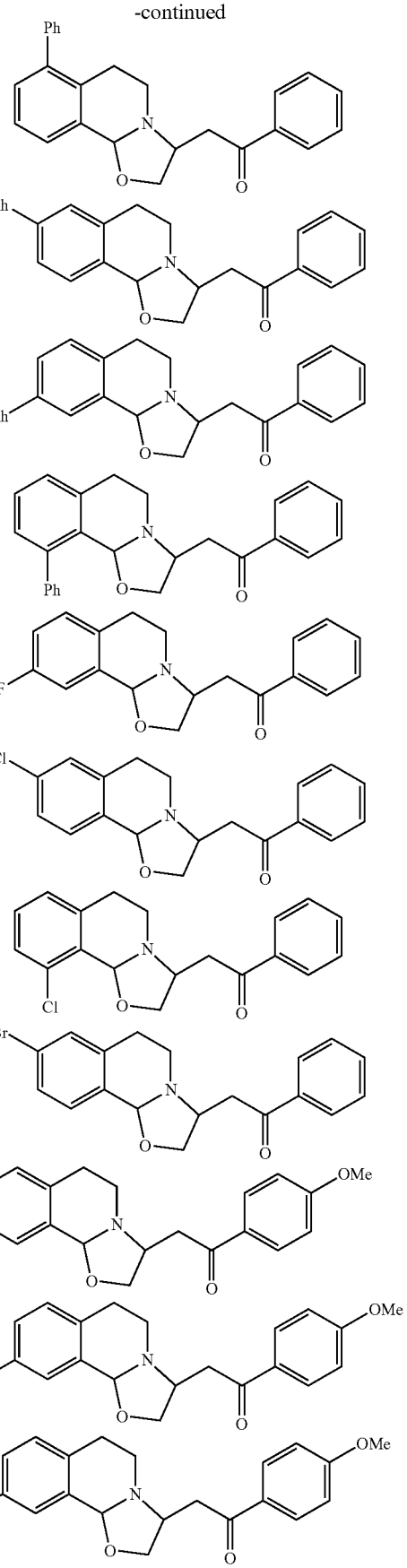

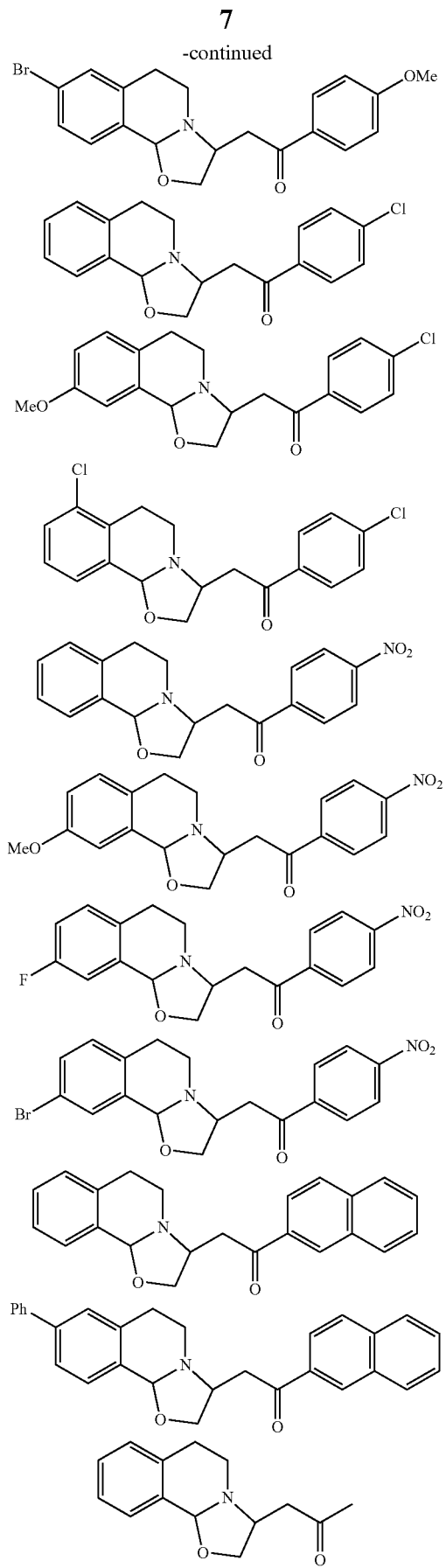
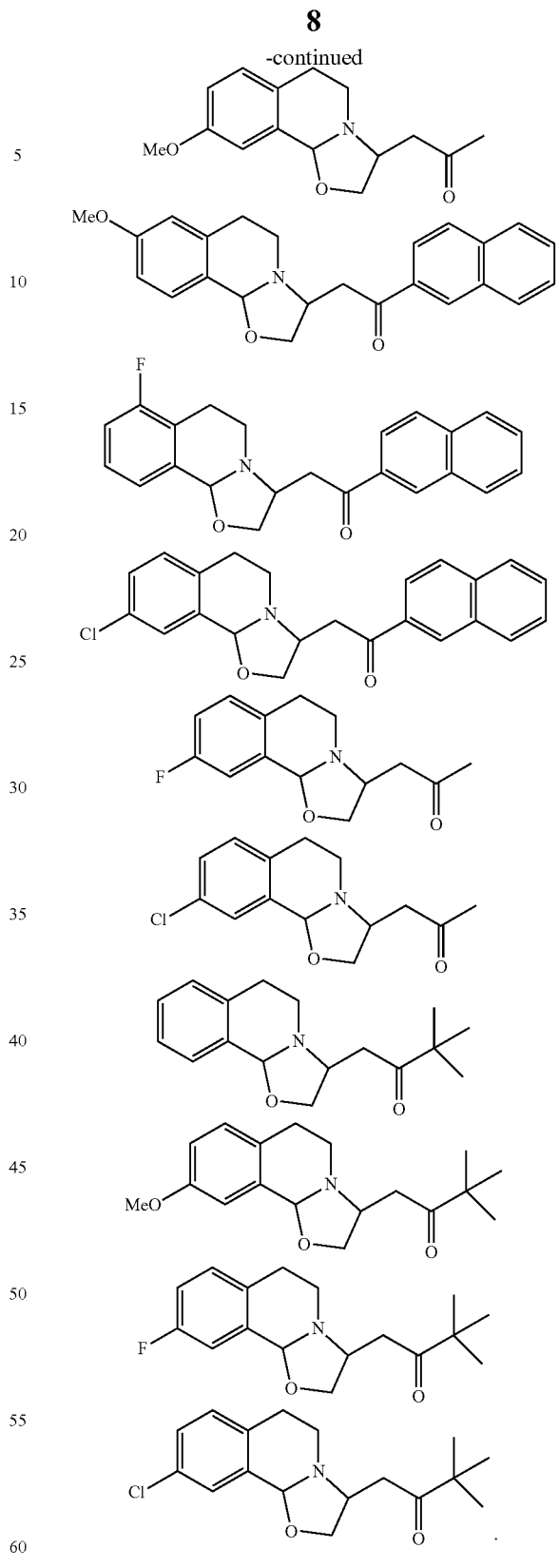
In an embodiment of the invention, the yield of the compound 1c ranges from 55% to 98%, and preferably ranges from 70% to 98%.
In an embodiment of the invention, when the compound 1a is a compound as shown in the following formula

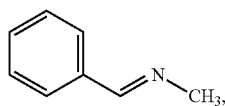

the compound 1c which is synthesized from the compound 1a and the compound 1b by reaction is selected from the following chemical structures:

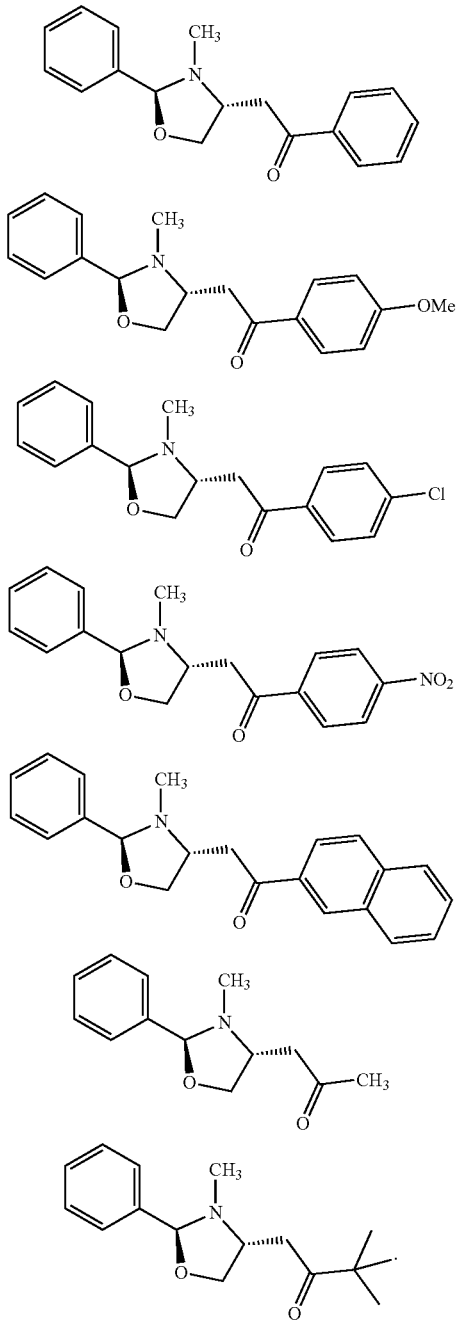

In an embodiment of the invention, the yield of the compound 1c ranges from 55% to 98%, and preferably ranges from 70% to 98%.

Then the technical characteristics and the connotation of the invention will be further described through specific experiment examples.

First Experiment Example

In the first experiment example of the invention, a compound 1a (3,4-dihydroisoquinoline) which comprises various substituent groups $R^1$ reacts with a compound 1b (methoxyl unsaturated ketones) with an electron donating characteristic on a benzene ring, and an equation is as follows:

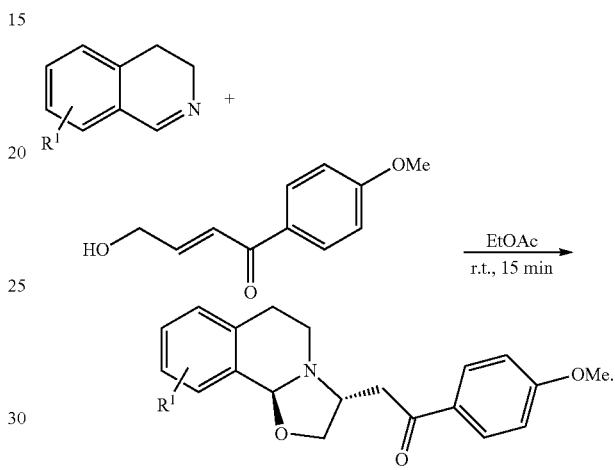

Following products 50ba to 50bg are obtained:

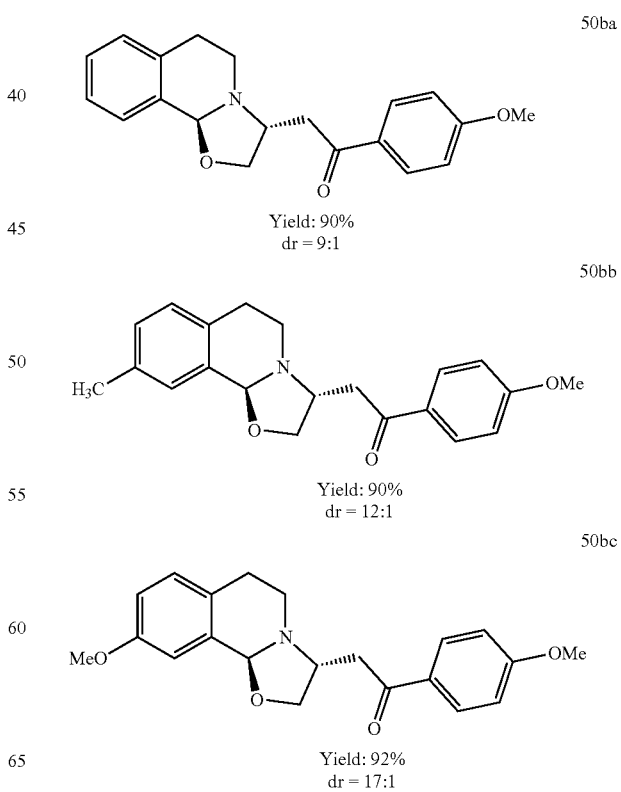

50ba

Yield: 90%
dr = 9:1

50bb

Yield: 90%
dr = 12:1

50bc

Yield: 92%
dr = 17:1

-continued

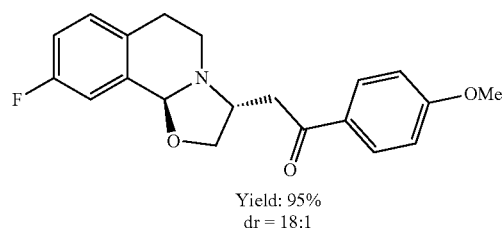

50bd

Yield: 95%
dr = 18:1

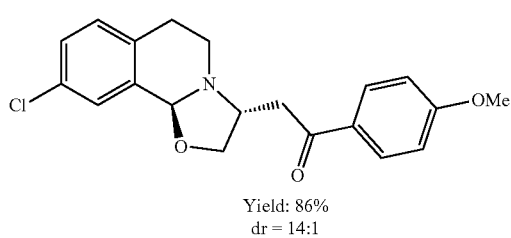

50be

Yield: 86%
dr = 14:1

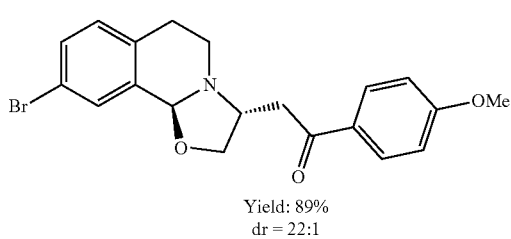

50bf

Yield: 89%
dr = 22:1

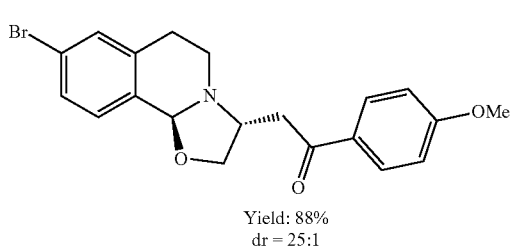

50bg

Yield: 88%
dr = 25:1

The yield of the compound 50ba of which a 3,4-dihydroisoquinoline ring does not have any substituent groups is 90%; when an electron pushing group exists, the yield is respectively 90% in 50bb of which the substituent group is methyl group and 92% in 50bc of which the substituent group is methoxyl; and when a substituent group on isoquinoline is halogen, the yield is respectively 95% in 50bd of which the substituent group is fluoro, 86% in 50be of which the substituent group is chloro, 89% in 50bf of which the substituent group is seventh-position bromo and 88% in 50bg of which the substituent group is sixth-position bromo.

To sum up, in the first example, the compound 1b with the electron pushing characteristic on the benzene ring is used as an initiator, when the benzene ring is connected to the electron pushing group, no matter whether a substituent group $R^1$ of the compound 1a is an electron pushing group or an electron pulling group, the yield of the products is quite high, diastereoselectivity (greater than or equal to 9:1) is excellent, and a ratio value of the diastereoselectivity is obtained from a 1H-NMR spectrum chart and an integral value of an H9 chiral center 5.3 ppm.

Second Experiment Example

In the second experiment example of the invention, a compound 1b with a benzene ring connected with a chlorine atom is used as an initiator, and the compound 1b reacts with a compound 1a with a different substituent group $R^1$, and an equation is as follows:

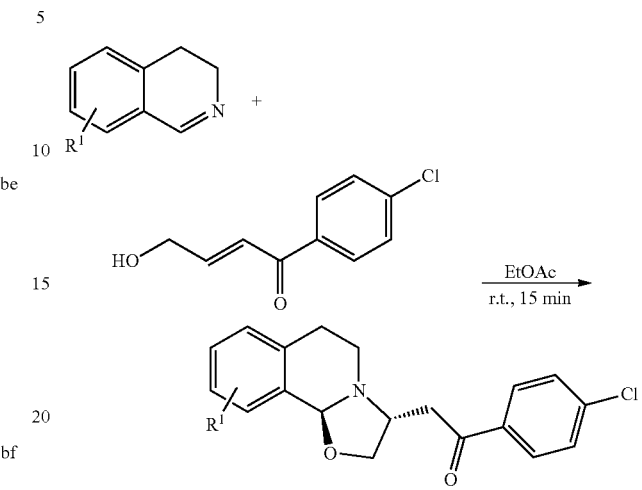

Following products 50ca-cg are obtained.

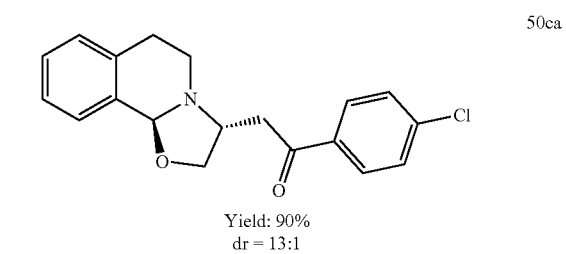

50ca

Yield: 90%
dr = 13:1

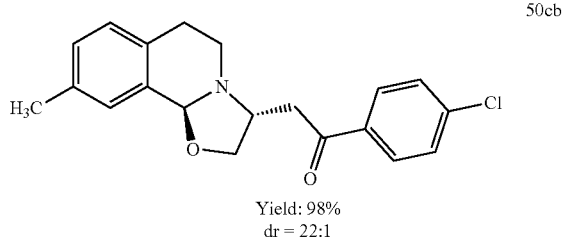

50cb

Yield: 98%
dr = 22:1

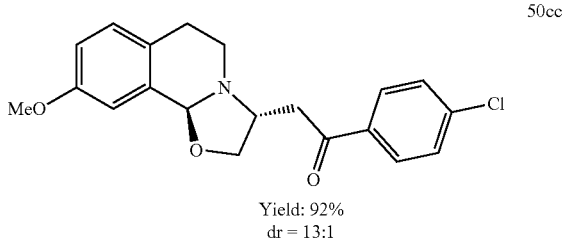

50cc

Yield: 92%
dr = 13:1

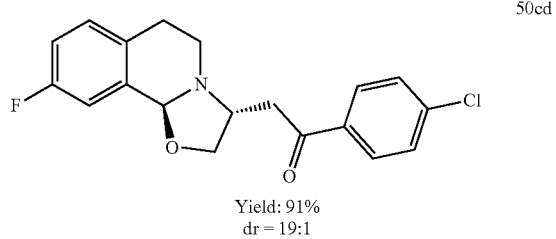

50cd

Yield: 91%
dr = 19:1

-continued

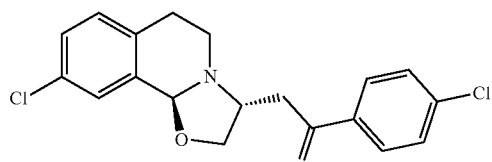
50ce

Yield: 95%
dr = 18:1

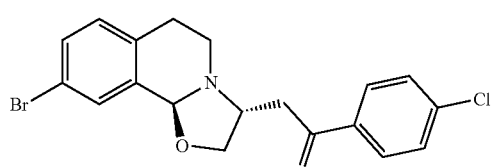
50cf

Yield: 85%
dr = 22:1

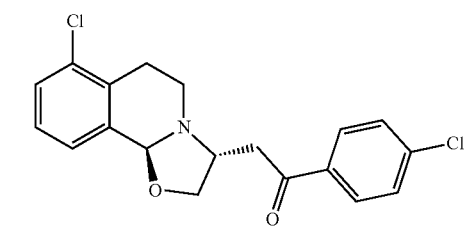
50cg

Yield: 90%
dr = 13:1

Through the products 50ca-cg, it can be discovered that the yield of 50ca which is not connected with any substituent groups is 90%; and when a substituent group is an electron pushing group, the yield is respectively 95% in 50cb of which the substituent group is methyl group and 92% in 50cc of which the substituent group is methoxyl; and when the substituent group is halogen, the yield is respectively 91% in 50cd of which the substituent group is fluoro, 95% in 50ce of which the substituent group is chloro, 85% in 50cf of which the substituent group is seventh-bit position bromo and 90% in 50cg of which the substituent group is fifth-position bit chloro. Therefore, when the benzene ring of the compound 1b is connected with an electron pulling group of chlorine, no matter whether the compound 1a is connected with an electron pushing group or an electron pulling group, the yield of the products is quite high, and diastereoselectivity (greater than or equal to 13:1) is excellent.

Third Experiment Example

In the third experiment example, a compound 1b with a substituent group on a benzene ring being a nitro is used as an initiator and reacts with a compound 1a with different substituent groups $R^1$, and an equation is as follows:

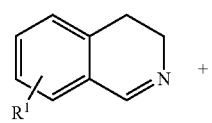
+

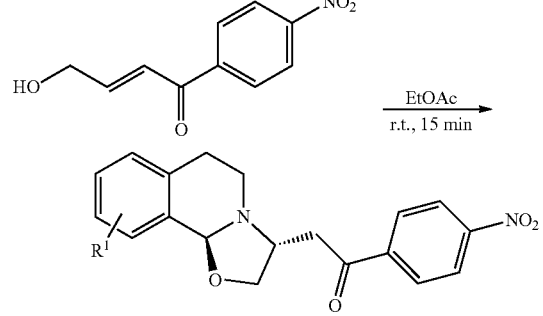

Following products 50da-df are obtained.

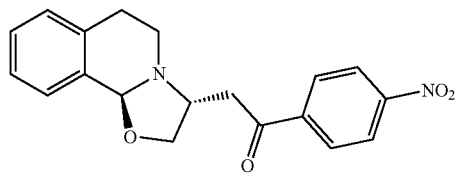
50da

Yield: 88%
dr > 25:1

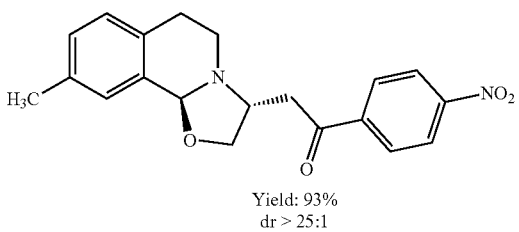
50db

Yield: 93%
dr > 25:1

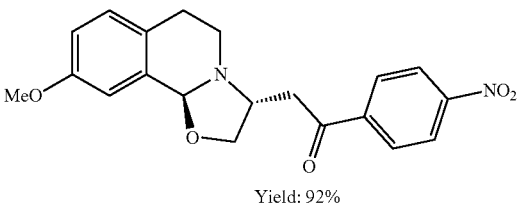
50dc

Yield: 92%
dr = 17:1

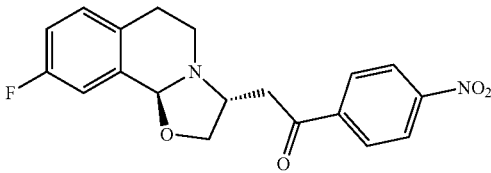
50dd

Yield: 90%
dr = 22:1

-continued

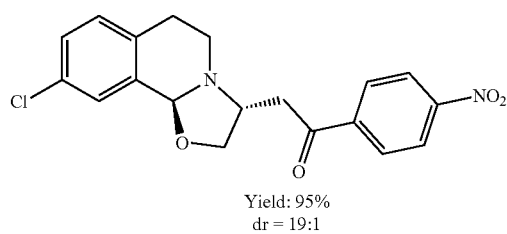

50de

Yield: 95%
dr = 19:1

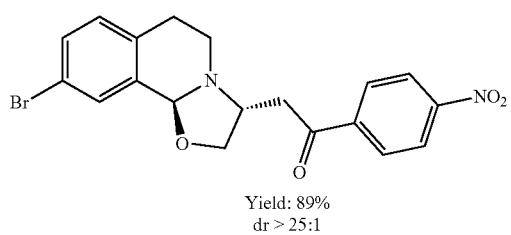

50df

Yield: 89%
dr > 25:1

Through the products 50da-df, it can be discovered that the yield of the product 50da without substituent groups is 88%. When a substituent group is an electron pushing group, the yield of 50db of which the substituent group is methyl group is 93%, and the yield of 50bc of which the substituent group is methoxyl is 92%; when the substituent group is halogen, the yield of 50bd of which the substituent group is fluoro is 90%, the yield of 50be of which the substituent group is chloro is 95%, and the yield of 50bf of which the substituent group is bromo is 89%. On the whole, the yield of reaction of the compound 1b which has nitro of a strong electron pulling group and the compound 1a with different substituent groups is generally high, and moreover, diastereoselectivity (greater than or equal to 25:1) is quite high.

Fourth Experiment Example

In the fourth experiment example of the invention, an unsaturated ketones initiator compound 1b with a substituent group $R^2$ as a methyl group or an isobutyl reacts with a compound 1a with different substituent groups 1a, and an equation is as follows:

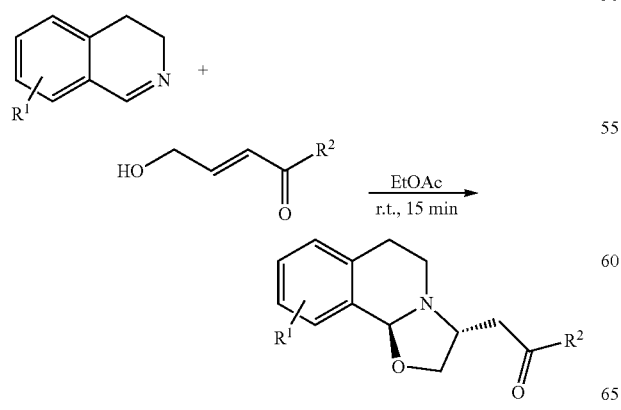

Following products 50fa-gf are obtained.

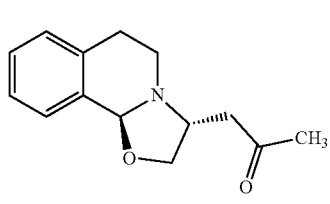

50fa

Yield: 92%
dr = 12:1

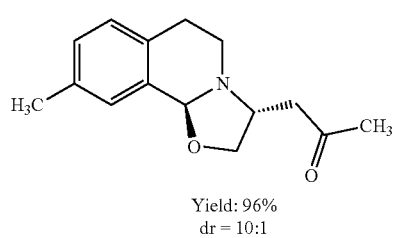

50fb

Yield: 96%
dr = 10:1

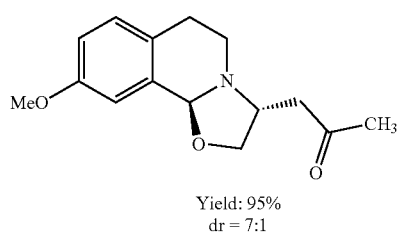

50fc

Yield: 95%
dr = 7:1

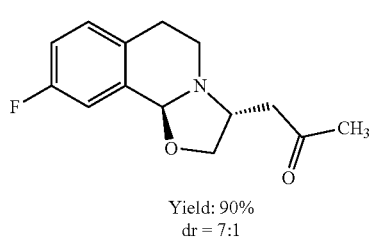

50fd

Yield: 90%
dr = 7:1

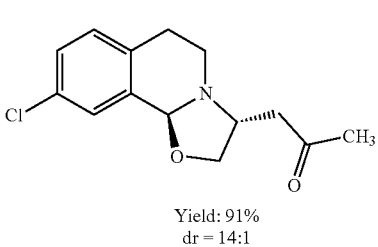

50fe

Yield: 91%
dr = 14:1

50ff

Yield: 91%
dr = 8:1

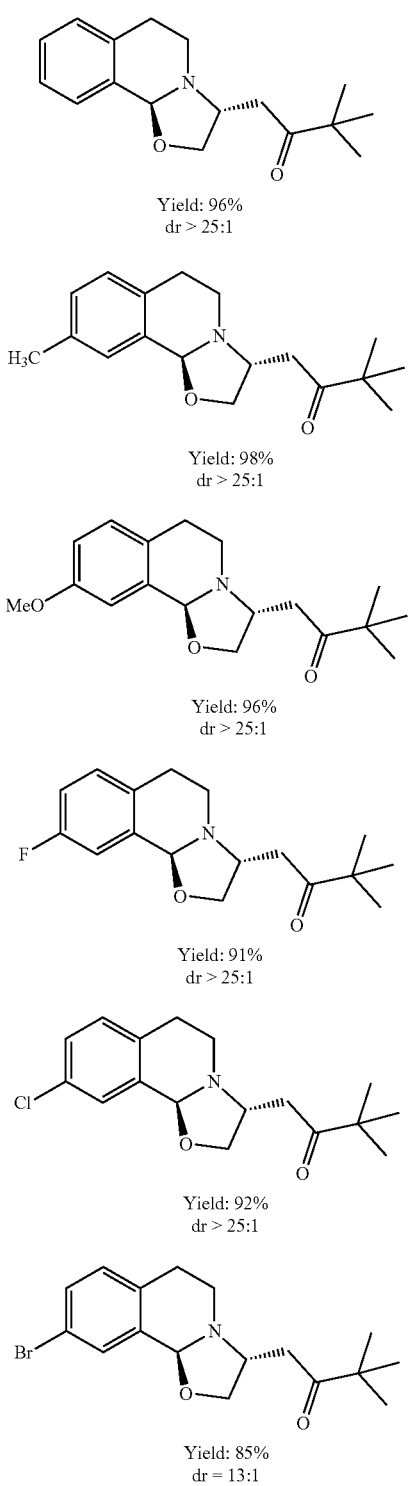

Through the products 50fa-gf, it can be discovered that the yields of the products are almost above 90% or above 95% and even reach 98% no matter whether the substituent group is an electron pushing group or an electron pulling group, and diastereoselectivity of the product obtained by reaction of the compound 1b with $R^2$ as a methyl group is slightly lower than that of the product obtained by reaction of the compound 1b with $R^2$ as a phenyl in the first experiment example and the second experiment example, but is still above 7:1; and diastereoselectivity of the product obtained by reaction of the compound 1b with $R^2$ as an isobutyl is higher than diastereoselectivity of the product obtained by reaction of the compound 1b with $R^2$ as a methyl group.

Fifth Experiment Example

Then, N-benzylidenemethylamine which is a ring opening compound is used as an initiating compound 1a and reacts with an unsaturated ketones initiator compound 1b substituted by different substituent groups. An equation is as follows:

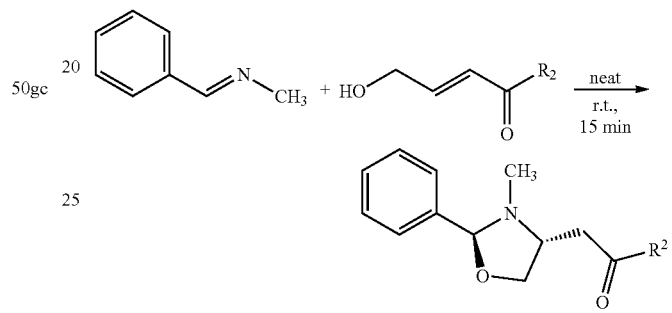

Following high-yield liquid products 56a-g are obtained.

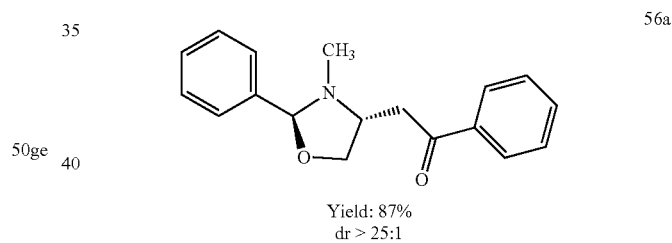

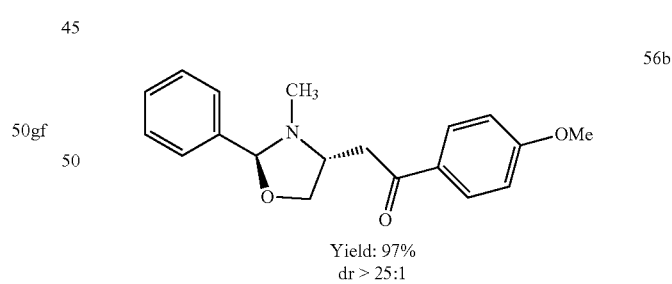

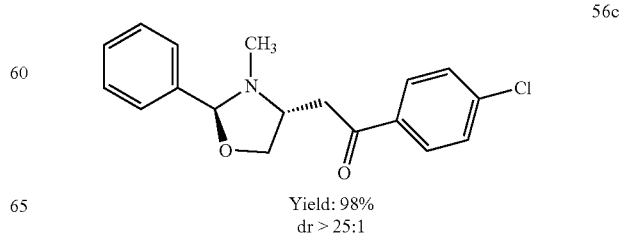

-continued

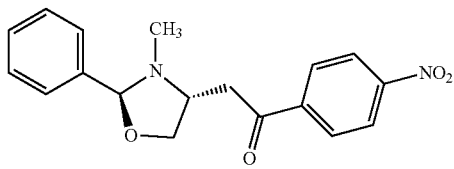

56d

Yield: 88%
dr > 25:1

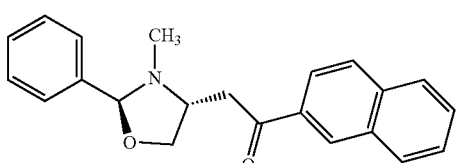

56e

Yield: 88%
dr > 25:1

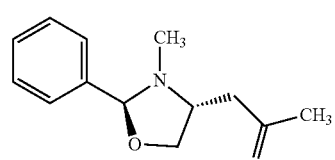

56f

Yield: 94%
dr > 25:1

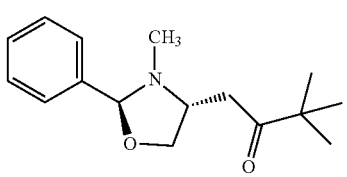

56g

Yield: 91%
dr > 25:1

In the fifth experiment example, because the compound 1a is a liquid compound with good flowability, reaction is carried out without under a solvent-free (Neat) substrate. After the compound 1a and the compound 1b are directly mixed added together and are stirred for 15 minutes at room temperature, whether the compounds are completely converted into the products or not is determined by spectrographical identification, the yield is 87-98%, and it proves that high-yield and high-purity ring-opening 1,3-oxazolidine derivatives 56a-g can be obtained without solvents and without any purification, signals of other groups of isomers are not observed in by 1H-NMR, and it shows that the reaction has quite high diastereoselectivity (greater than or equal to 25:1). It may be added that in other patterns of this embodiment, reaction can be selectively carried out in a proper solvent depending on the circumstances as needed, and the solvent, for example, can be selected from a group consisting of methylbenzene, ethyl acetate, ether, water, methanol, ethanol, butanol and a combination thereof, and is ethyl acetate preferably.

Sixth Experiment Example

In order to confirm the practical value of reaction of the invention, reacting dose of original initiators 1a and 1b are increased to be 12.7 mole from 0.76 mole, gram is used as a unit to observe reactivity after the reacting dose is increased, after the original initiators 1a and 1b react for 15 minutes at room temperature, a following product is generated, and an equation is as follows.

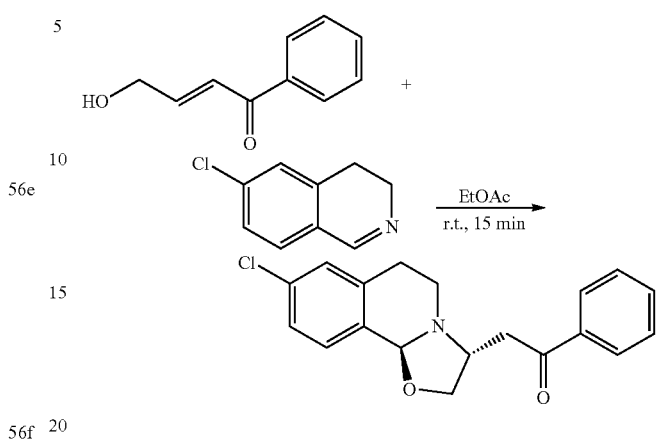

The yield of a product obtained after recrystallization is 85%, and is little different from the yields (91%) when the reacting dose of the initiators 1a and 1b is 0.76. It proves that by the method, reactivity is not affected even when a large number of products are synthesized, reaction is carried out at normal temperature and under normal pressure, and therefore, the method has great potential in the aspect of industrial application.

Seventh Experiment Example

A triphenyl phosphine initiator (51) and 1,4-dioxane-2,5-diol (52) are heated in an anhydrous environment by using tetrahydrofuran as a solvent, are subjected to reflux reaction for 3 hours, and then are subjected to Wittig reaction, and an equation is as follows:

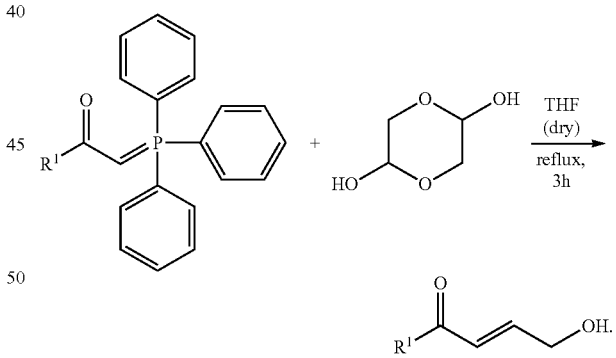

After column chromatography, following gamma-hydroxyl-alpha,beta-unsaturated ketones (30a-g) with different substituent groups can be obtained.

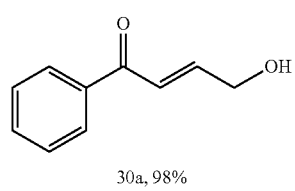

30a, 98%

-continued

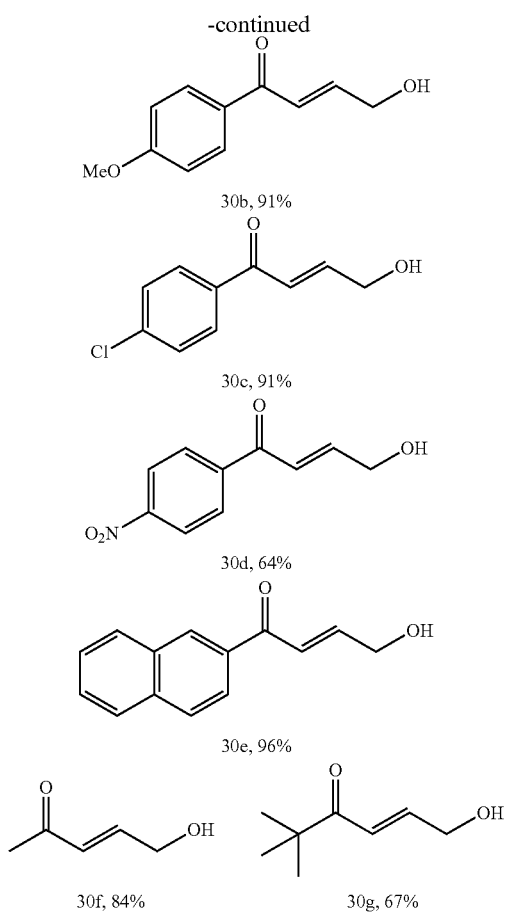

Then, reaction conditions are researched by selecting the gamma-hydroxyl-alpha,beta-unsaturated ketone 30a and 3,4-dihydroisoquinoline without substituent groups as standard models of reaction.

Types of solvents used in various groups, presence or absence of additives, reaction time and yields are shown in the following table 1, and the following reactions are all carried out at room temperature.

TABLE 1

| Group | Solvent | Additive | Reaction time | Yield (%) |
|---|---|---|---|---|
| 1 | Methylbenzene | Acetic acid | 1 hour | 76 |
| 2 | Methylbenzene | — | 1 hour | 73 |
| 3 | Methylbenzene | — | 3 hours | 76 |
| 4 | Methylbenzene | Acetic acid | 15 minutes | 75 |
| 5 | Methylbenzene | — | 15 minutes | 73 |
| 6 | Ethyl acetate | Acetic acid | 15 minutes | 93 |
| 7 | Ethyl acetate | — | 15 minutes | 93 |
| 8 | Ethyl ether | — | 15 minutes | 83 |
| 9 | Water | — | 15 minutes | 75 |
| 10 | Methanol | Acetic acid | 15 minutes | 71 |
| 11 | Methanol | — | 15 minutes | 73 |
| 12 | Ethanol | — | 15 minutes | 63 |
| 13 | 1-butanol | — | 15 minutes | 73 |
| 14 | Dimethylformamide (DMF) | — | 15 minutes | 55 |

Comparing group 1 with and group 2 in table 1, when the methylbenzene is used as a solvent, whether the acetic acid with the concentration of 15 mol % is added as an additive or not added does not affect the final yield. In order to comfirm the above situation again, the reaction time is prolonged to be 3 hours under the condition that the additive is not added, but the yield (group 3) is not improved remarkably (group 3).

Then, in the group 4 and the group 5, the reaction time is observed by thin layer chromatography, and it is discovered that reaction is finished after stirring is carried out for 15 minutes at room temperature no matter whether the additive is added or not, and the yields of the group 4 and the group 5 are only slightly different from the yields of the group 1 and the group 2 in which stirring is carried out for 1 hour.

In order to achieve environmental friendliness to conform to the advantage of green chemistry, the ethyl acetate (groups 6 and 7), the ethyl ether (group 8), the water (group 9), the methanol (groups 10 and 11), the ethanol (group 12), the 1-butanol (group 13) and the dimethylformamide (group 14) which have low toxicity are selected in other examples, however, like the previous groups 1 and 2, the final yields (groups 6 and 7) cannot be affected no matter whether the additive is added or not on the premise that the same solvent is used, and selection of the solvent may affect the yields. In a preferable example in the invention, the ethyl acetate is used as a solvent, and the yield can reach 93%.

To sum up, in the prior art, synthesis needs to be carried out in a strict environment or in virtue of adding a catalyst, thus obtaining satisfactory yield; but the method does not need to be carried out in the strict environment and does not need the catalyst, the yield is satisfactory, and the tetrahydroisoquinoline oxazolidine can be synthesized at normal temperature and under normal pressure by relatively few steps within short time. Therefore, compared with the known art, the method not only has lenient synthesis conditions, and also has quite simple synthesis steps, thus the synthesis cost can be effectively reduced, and the method also conforms to the currently promoted green chemical chemistry concept.

Only one preferred embodiment of the invention has been described above in detail, and cannot limit the implementation scope of the invention. That is, equivalent alternations and modifications made according to the application scope of the invention shall still fall within the claimed scope of the invention.

What is claimed is:
1. A method for synthesizing tetrahydroisoquinoline oxazolidine of compound 1c which is selected from the following chemical structures:

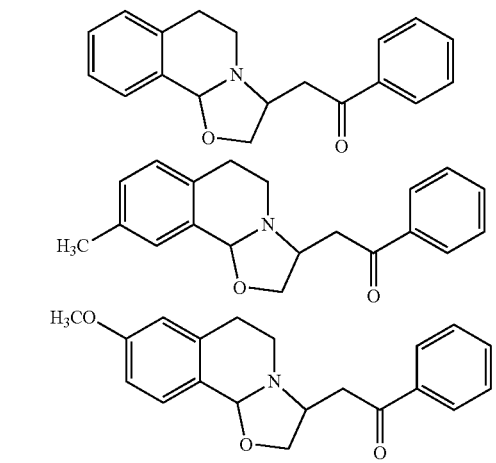

-continued
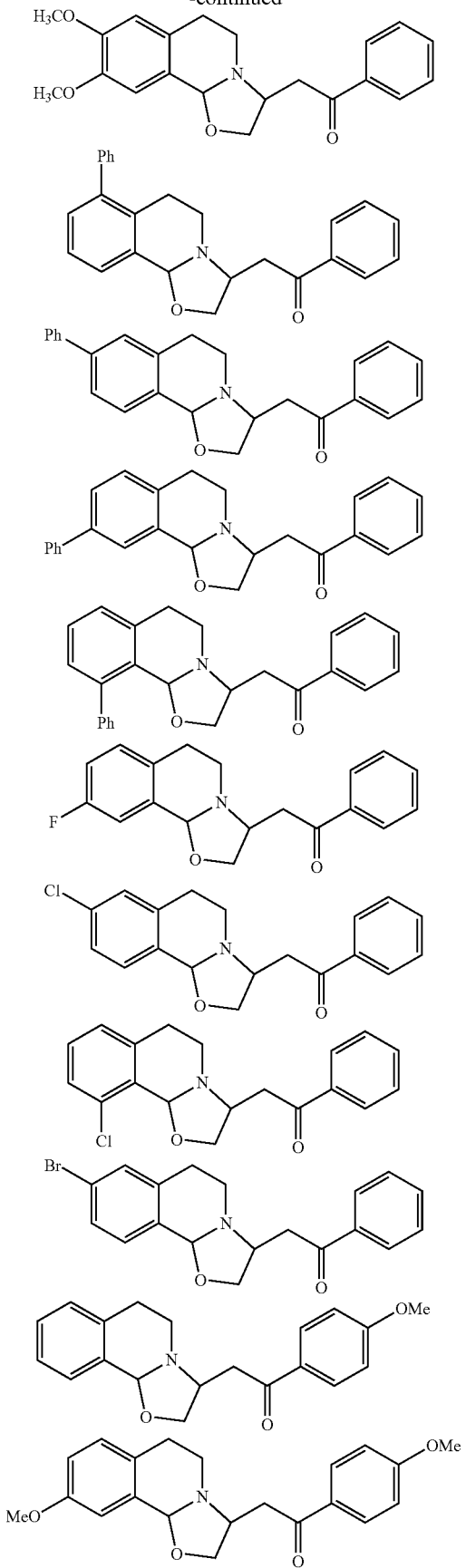
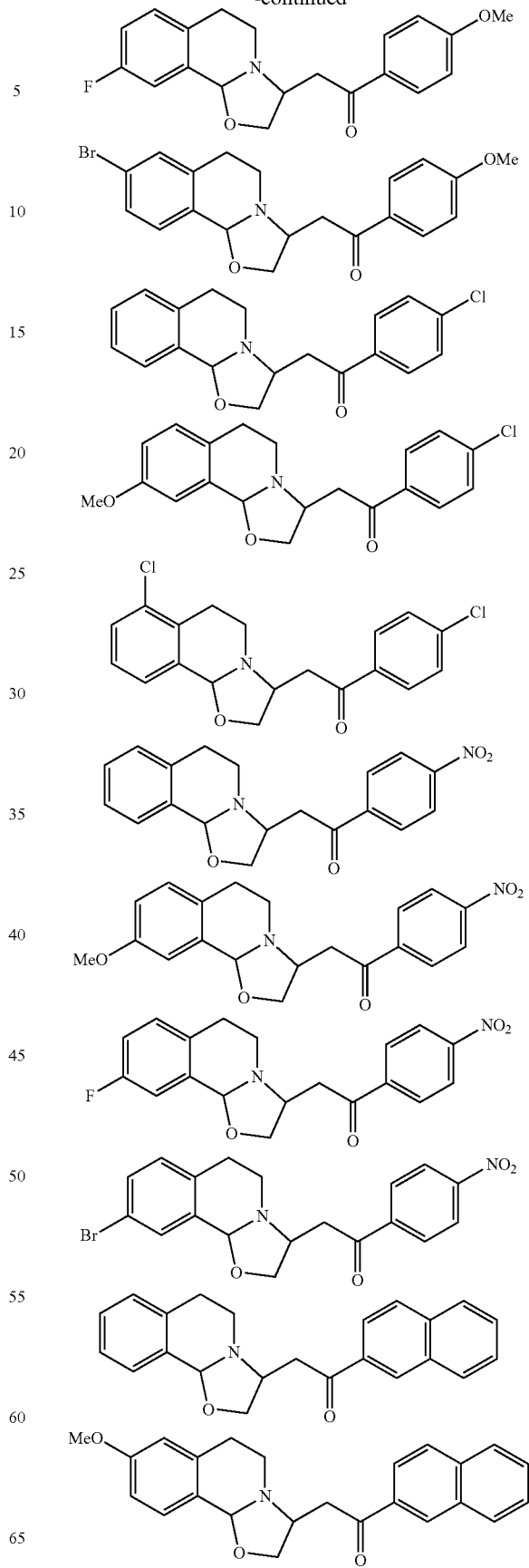

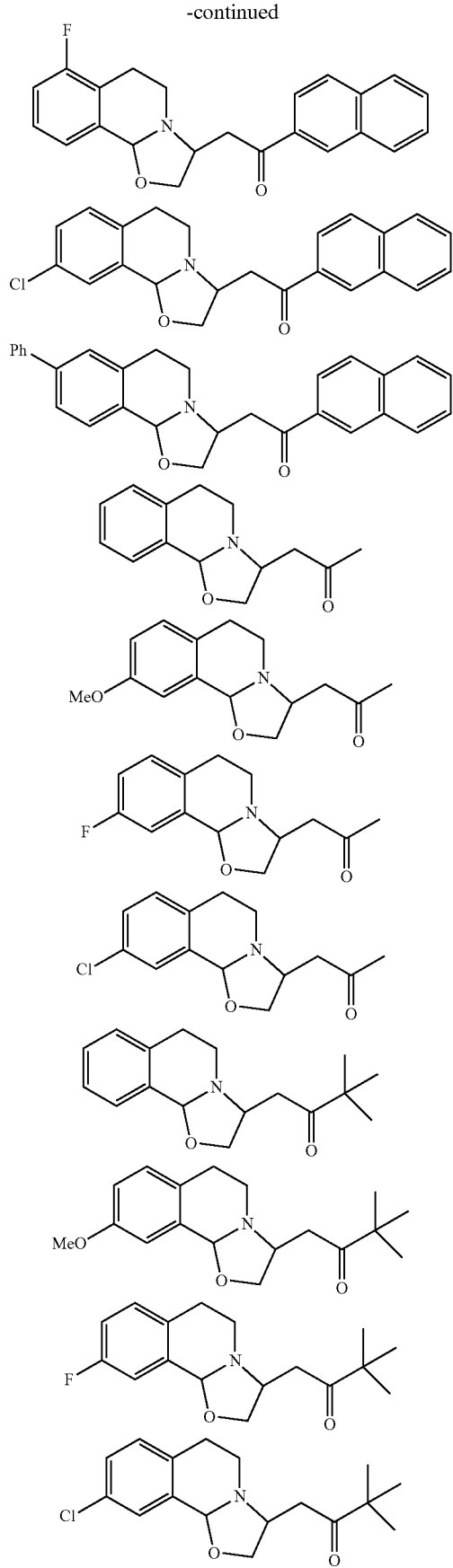
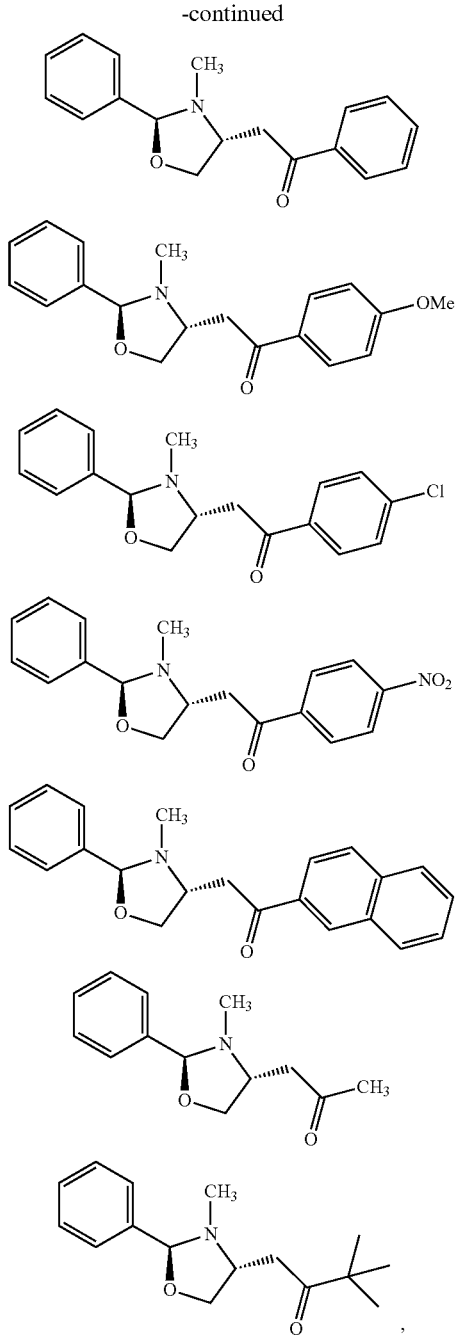
comprising: reacting a compound 1a with a compound 1b, wherein the compound 1a is
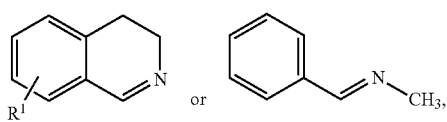
$R^1$ is hydrogen, halogen, methyl group, alkoxy group or phenyl the compound 1b is

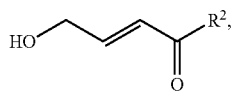

R² is selected from a substituted or unsubstituted phenyl, a substituted or unsubstituted naphthalene, a substituted or unsubstituted straight chain alkyl, a substituted or unsubstituted straight chain alkenyl, a substituted or unsubstituted straight chain alkynyl, a substituted or unsubstituted branched chain alkyl, a substituted or unsubstituted branched chain alkenyl, or a substituted or unsubstituted branched chain alkynyl; and the method is carried out at room temperature between 20° C. and 35° C.

2. The method for synthesizing tetrahydroisoquinoline oxazolidine according to claim 1, wherein R² is a phenyl substituted by a substituent group, and the substituent group is selected from at least one of a group consisting of an alkoxy group, halogen, a nitro and a combination thereof.

3. The method for synthesizing tetrahydroisoquinoline oxazolidine according to claim 1, wherein reaction time ranges from 10 minutes to 3 hours.

4. The method for synthesizing tetrahydroisoquinoline oxazolidine according to claim 1, wherein the compound 1a and the compound 1b react according to an equivalent proportion of 1:1.

5. The method for synthesizing tetrahydroisoquinoline oxazolidine according to claim 1, wherein the method further comprises: adding an additive, which is acetic acid.

6. The method for synthesizing tetrahydroisoquinoline oxazolidine according to claim 1, wherein the reaction is carried out in a solvent when the compound 1a is as shown in the following formula, and the solvent is selected from a group consisting of methylbenzene, ethyl acetate, ether, water, methanol, ethanol, butanol and a combination thereof:

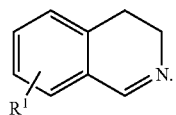

7. The method for synthesizing tetrahydroisoquinoline oxazolidine according to claim 6, wherein a compound 1c synthesized from the compound 1a and the compound 1b by reaction is selected from the following chemical structures:

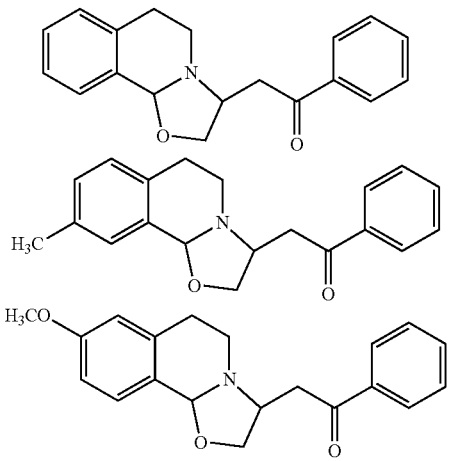

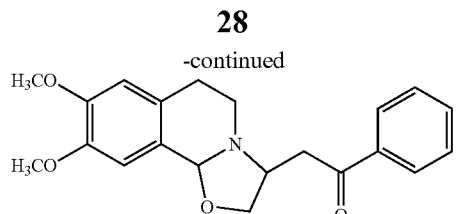

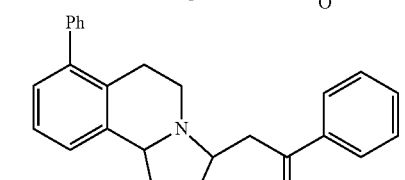

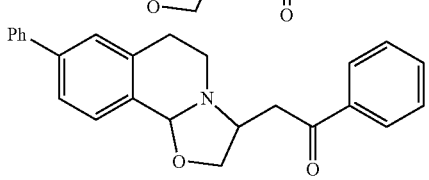

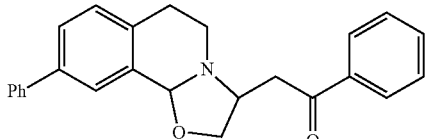

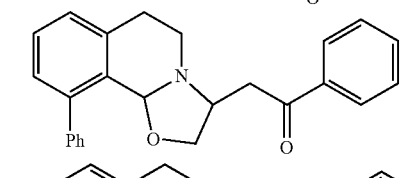

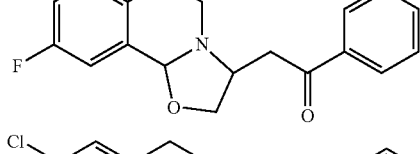

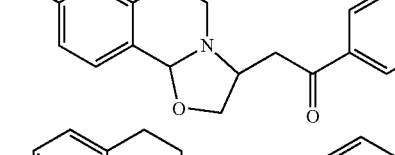

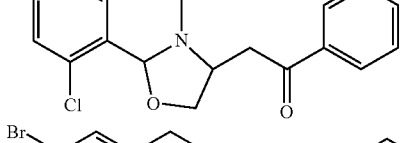

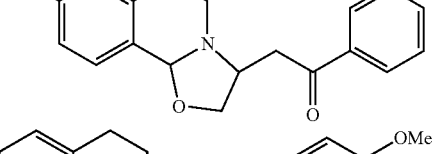

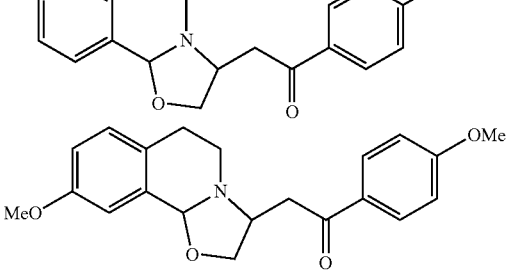

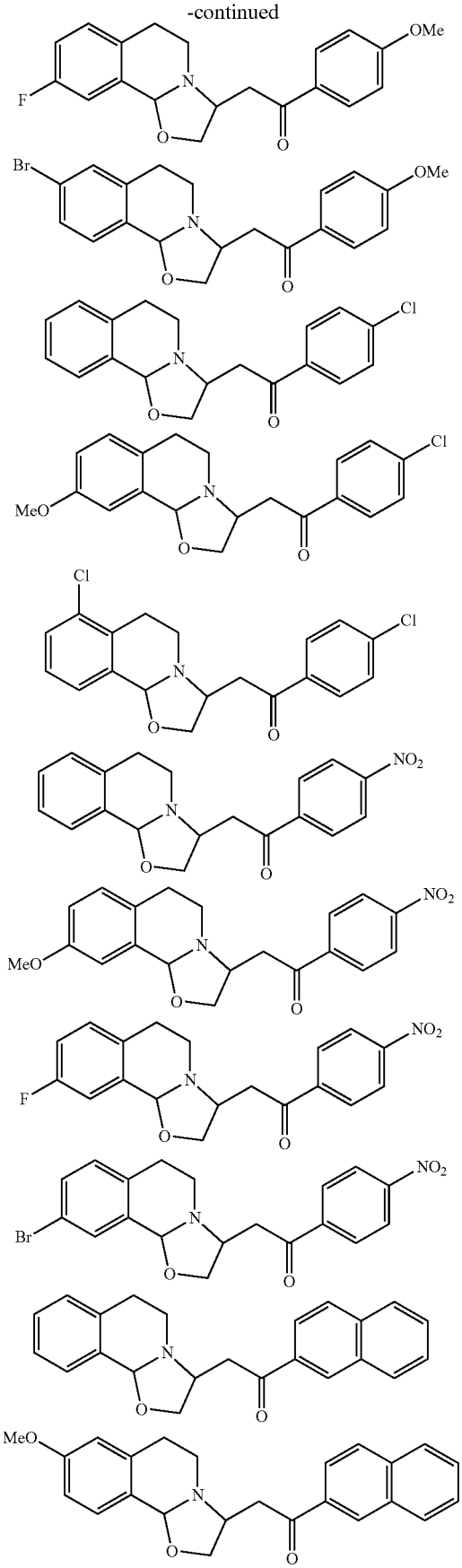
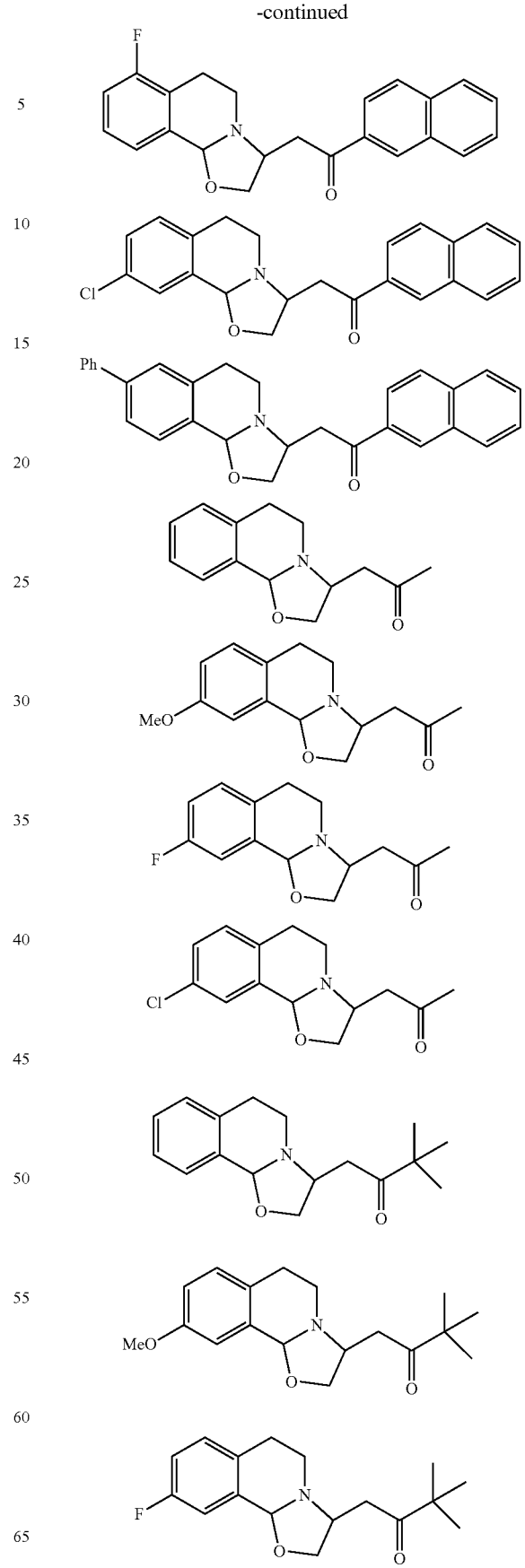

-continued

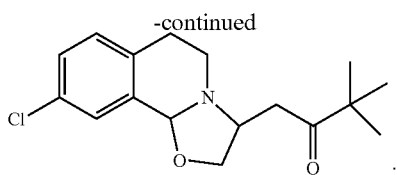

8. The method for synthesizing tetrahydroisoquinoline oxazolidine according to claim 7, wherein the yield of the compound 1c ranges from 55% to 98%.

9. The method for synthesizing tetrahydroisoquinoline oxazolidine according to claim 1, wherein when the compound 1a is as shown in the following formula

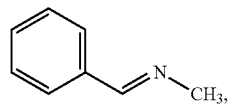

the compound 1c which is synthesized from the compound 1a and the compound 1b by reaction is selected from the following chemical structures:

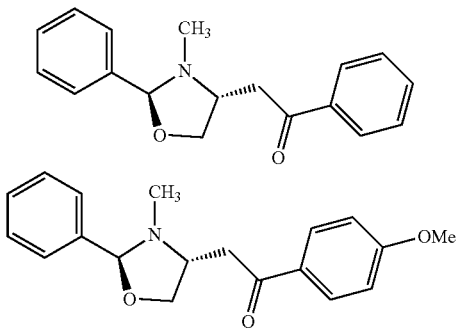

-continued

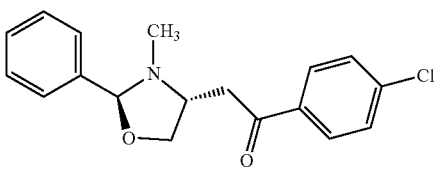

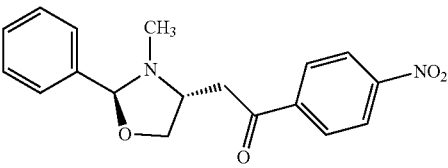

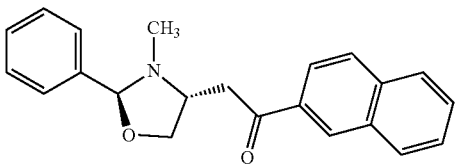

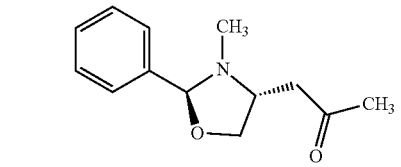

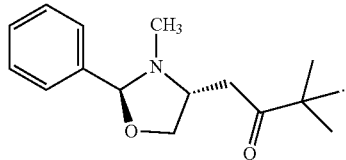

10. The method for synthesizing tetrahydroisoquinoline oxazolidine according to claim 9, wherein the yield of the compound 1c ranges from 55% to 98%.

\* \* \* \* \*